(12) United States Patent
Stauffer

(10) Patent No.: US 6,330,479 B1
(45) Date of Patent: Dec. 11, 2001

(54) MICROWAVE GARMENT FOR HEATING AND/OR MONITORING TISSUE

(75) Inventor: Paul R. Stauffer, San Rafael, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/455,303

(22) Filed: Dec. 6, 1999

Related U.S. Application Data

(60) Provisional application No. 60/111,148, filed on Dec. 7, 1998.

(51) Int. Cl.[7] .......................................... A61F 2/00
(52) U.S. Cl. .............................. 607/101; 607/96; 607/154; 607/156
(58) Field of Search ......................... 607/96–99, 101–102, 607/104, 154, 155

(56) References Cited

U.S. PATENT DOCUMENTS

| | | | |
|---|---|---|---|
| 4,197,851 | * | 4/1980 | Fellus . |
| 4,332,260 | * | 6/1982 | Bicher et al. . |
| 4,397,313 | | 8/1983 | Vaguine . |
| 4,528,991 | * | 7/1985 | Dittmar et al. . |
| 4,672,980 | * | 6/1987 | Turner . |
| 4,932,420 | * | 6/1990 | Goldstein . |
| 4,974,587 | | 12/1990 | Turner et al. . |
| 5,101,836 | | 4/1992 | Lee . |
| 5,503,150 | | 4/1996 | Evans . |
| 5,631,446 | * | 5/1997 | Quan .................................... 174/254 |
| 5,769,879 | | 6/1998 | Richards et al. . |

* cited by examiner

Primary Examiner—Roy Gibson
(74) Attorney, Agent, or Firm—Townsend and Townsend and Crew LLP

(57) ABSTRACT

A flexible microwave applicator and method of use thereof. The applicator includes a flexible, dielectric-containing compartment (e.g. temperature regulated water or oil) having a variable contour, tissue-engaging surface and an opposite non-tissue-engaging surface and an antenna array adjacent to a non-tissue-engaging surface. The antenna array includes at least one flexible printed circuit board having a front metal surface, a dielectric substrate, a back metal surface, a connection structure for connecting the antenna array to at least one external microwave device, at least one dual concentric conductor aperture on the front surface, and at least one microstrip feedline in communication with the dual concentric conductor aperture and the connection structure. The microwave applicator also includes flexible attachment material for placement over the antenna array and dielectric compartment to allow the microwave applicator to be attached to a subject like a garment which closely conforms to the anatomy portion to be heated. The flexible attachment material may be configured such that the microwave applicator is configured as an appropriately-shaped type of garment, for example, a vest, jacket, cap, hood, blanket, custom shaped conformal wrap, sleeve, or as a pair of shorts.

60 Claims, 11 Drawing Sheets

MICROWAVE GARMENT FOR HEATING AND/OR MONITORING TISSUE

This appln. claims benefit of Prov. No. 60/111,148 filed Dec. 7, 1998.

BACKGROUND OF THE INVENTION

1. Field of the Invention

The present invention relates generally to applying microwaves to a material, and more particularly, to a flexible microwave array that can conform closely to complex curvatures of the human body for uniform heat treatment of superficially located tumors or benign skin conditions.

2. Description of the Prior Art

The use of microwave applicators for hyperthermia treatment of superficial tumors is well known. However, difficulties have been encountered in applying such devices to large areas with complex curvatures, such as in the neck and chest area, since the patients must, while retaining the antenna(s) of the microwave applicator in an evenly spaced perpendicular alignment with the surface of the skin, maintain proper inter-antenna spacing in order to facilitate uniform heat treatment. Generally, these microwave applicators are capable of heating areas of superficial tissue for treatment of skin and superficial tissue related diseases such as chestwall recurrence of breast carcinoma, psoriasis or other non-cancerous skin conditions that can benefit from tissue reoxygenation, or increased blood perfusion and blood vessel permeability.

Hyperthermia, which consists of heating tumors at a temperature of 42–45∞ C for about one hour, has been shown capable of enhancing the affects of common anti-cancer treatments such as radiotherapy and chemotherapy. Effective heat treatment for superficial disease requires an applicator capable of treating irregularly shaped and often widespread disease extending from the skin surface to a maximum depth of about 1 cm. While previously used microwave applicators operating at either 915 or 433 MHz have demonstrated appropriate penetration of Specific Absorption Rate (SAR) for generating effective heating down to a maximum depth of 1–1.5 cm, treatment of the entire lateral extent of disease is usually impossible due to limited applicator size and poor coupling of the rigid planar structures of previous microwave applicators to the skin surface. Because superficial tissue disease often wraps around complex body contours, the applicator must be thin and flexible for complete, closely conforming coverage of various-sized areas as well as lightweight for patient comfort during long treatments.

Thus, previous microwave applicators generally have been inadequate for treating many types of superficial tumors, such as chestwall recurrence of breast carcinoma, skin cancer, psoriasis, and other skin conditions, due to their large, bulky size as well as their generally inflexible, planar arrangement.

SUMMARY OF THE INVENTION

The present invention addresses the shortcomings of the prior art. A novel microwave applicator in accordance with the present invention is ideally suited for applying microwaves to skin and superficial tissue and thus is capable of uniformly heating large areas of superficial tissue over contoured anatomy for treatment of skin and superficial tissue related disease, such as chestwall recurrence of breast carcinoma, or for the diagnosis or treatment of other skin conditions that can benefit from tissue reoxygenation or increased blood perfusion and blood vessel permeability. In addition, other applications may benefit from this applicator's ability to rapidly and uniformly heat large areas of skin and underlying tissue, or from the potential to concentrate microwave power deposition in specific tissue heterogeneities like freckles, hair follicles, scars or tiny tumor nodules. The present invention provides a microwave applicator that can facilitate treatments of, for example, plaque psoriasis, stimulation of bone growth, healing of superficial cuts and abrasion wounds, or concentration of the delivery or heat activation of gene therapy, liposomes, or contrast agents for improved CT or MR Imaging of superficial tissues. Additionally, the microwave applicator may be used to warm surgically exposed organs. Also, the microwave applicator may be configured as an intracavitary applicator to be placed within a body cavity and thus treat tissue and organs located within 1–1.5 cm distance of the cavity wall.

In accordance with one aspect of the present invention, a flexible microwave applicator for heating areas of superficial tissue over contoured anatomy includes a flexible, fluid-retaining compartment having a tissue-engaging surface and an opposite non-tissue-engaging surface. The applicator further includes an antenna array adjacent to the non-tissue-engaging surface that includes at least one flexible printed circuit board having a front metal surface, a dielectric substrate, a back metal surface, and connection apparatus for connecting the antenna array to a power source. At least one dual concentric conductor radiating aperture is included on the front surface and at least one microstrip feed line is included that is in communication with the dual concentric conductor radiating aperture and the connection apparatus. Finally, the microwave applicator includes a flexible attachment material for placement over the antenna array and fluid compartment to allow the microwave applicator to be securely attached to a subject.

In accordance with another aspect of the present invention, the antenna array includes a plurality of dual concentric conductor radiating apertures on the front surface and a plurality of microstrip feedlines in communication with the dual concentric conductor apertures and the connection apparatus.

In accordance with a further aspect of the present invention, the microwave applicator is capable of non-invasively monitoring the temperature of the superficial tissue. In one embodiment, monitoring of the temperature of the superficial tissue is accomplished by providing at least one plastic catheter molded into the tissue-engaging surface and at least one sensor that is placed within or pulled repeatedly through the catheter. In another embodiment, non-invasive temperature measurements of superficial tissue under the applicator are accomplished through radiometric monitoring of temperature dependent signals emanating from the tissue and received by an antenna structure located on the flexible circuit board.

In accordance with various aspects of the present invention, the flexible attachment material is configured such that the microwave applicator is configured in various garment-like forms such as, for example, a vest, a jacket, a blanket or wrap, a sleeve, a cap or hood, or a pair of shorts.

In accordance with yet a further aspect of the present invention, the fluidretaining compartment has a relatively thin thickness in a range of 0.25 cm to 2.5 cm, more preferably in a range of 0.5 cm to 1.5 cm, and most preferably, the housing has a thickness of about 0.5 cm.

Accordingly, the present invention provides a flexible microwave applicator that is capable of being configured to the contour of the anatomy of a patient easily and comfortably. Each dual concentric conductor aperture heats effectively across its face to just outside its perimeter to allow for the apertures to be placed in arrays for uniform heating of large surface areas with generally no hot or cold spots between adjacent apertures. Arbitrarily large antenna arrays may be manufactured inexpensively using ultra-thin and flexible PCB technology that can be wrapped in close conformance around highly contoured patient anatomy. Such a thin PCB array along with the relatively thin flexible fluid-retaining housing or dielectric bolus structure, produces a lightweight heat applicator for improved patient comfort. The outer flexible attachment material, generally an elastic garment, secures the applicator comfortably in place on the patient and allows the patient to sit and/or move short distances around the power source during heat treatment, rather than the prior art's previous restriction to a prone position that generally becomes uncomfortable for patients after less than one hour. This improved patient comfort during treatment helps facilitate longer treatment times, in comparison to prior microwave applicators. Such longer treatment times may be beneficial for new heat plus chemotherapy infusion protocols or to deliver higher thermal doses than has been possible previously. Finally, the thin, flexible microwave applicator in accordance with the present invention is generally electrically invisible to radiation such that external beam radiation therapy may be applied simultaneously with microwave heat for optimum interaction of heat and radiation.

Other features and advantages of the present invention will be understood upon reading and understanding the detailed description of the preferred exemplary embodiments, found herein below, in conjunction with reference to the drawings, in which like numerals represent like elements.

DESCRIPTION OF THE PREFERRED EXEMPLARY EMBODIMENTS

Figure 1A:
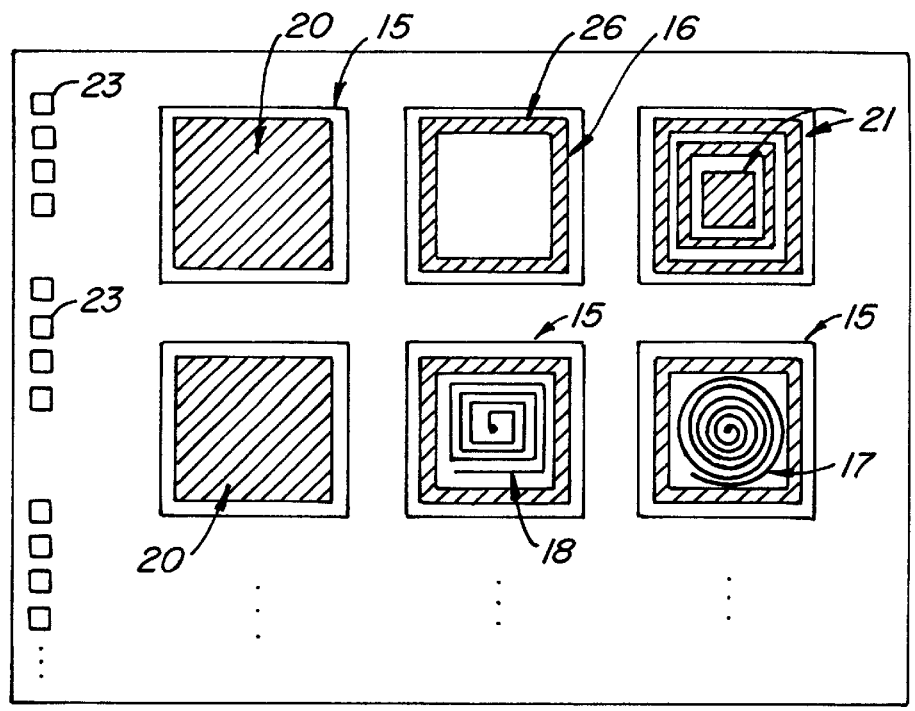
FIG. 1A is a front elevation view of a printed circuit board for use with the present invention.
Figure 1B:
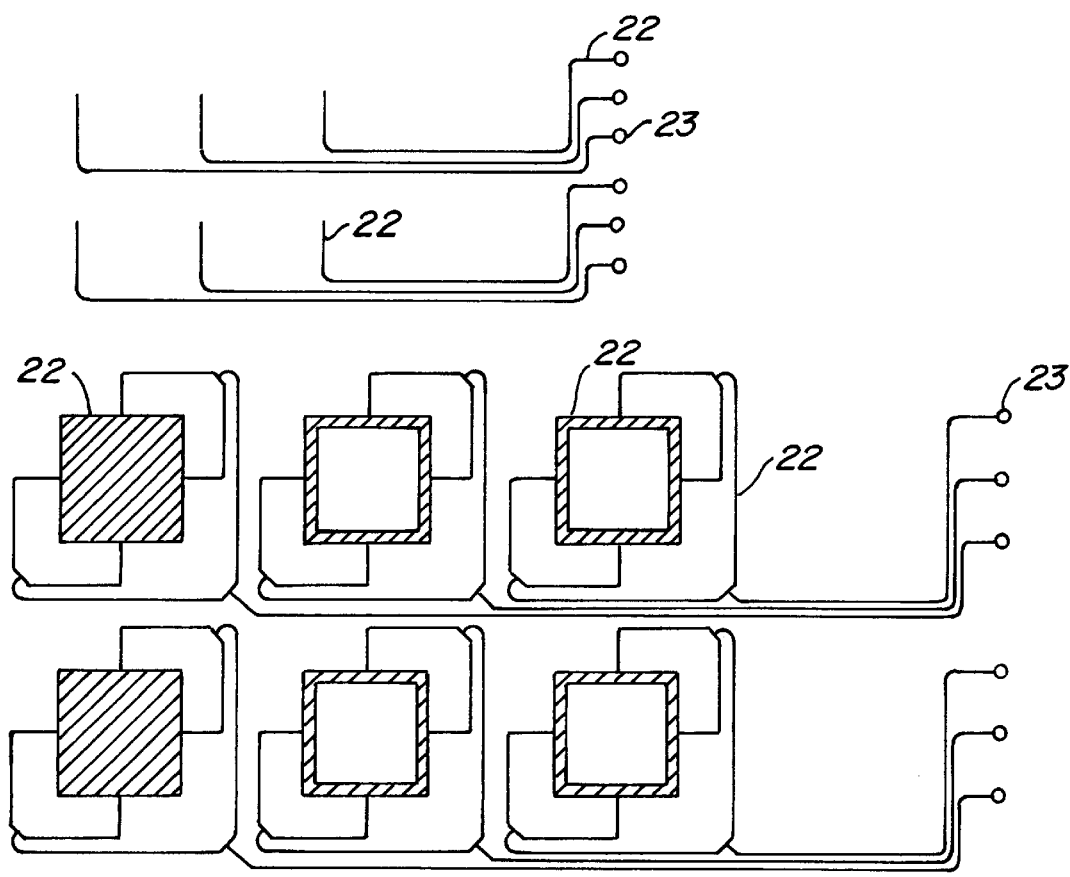
FIG. 1B is a back elevation view of the printed circuit board illustrated in FIG. 1A.

With reference to the drawings, a flexible conformal microwave applicator 10 in accordance with one embodiment of the present invention is illustrated. The applicator includes a flexible dielectric containing compartment 11, commonly referred to as a bolus. Preferably, compartment 11 is comprised of transparent soft and flexible vinyl filled with a fluid dielectric. Preferably two hoses 12 and 13 extend to the housing to provide a flow of water, or other dielectric fluid, which serves as a coolant and temperature control for both the applicator 10 and a surface (e.g. tissue) being heated by the applicator. The dielectric could be a non-fluid but flexible dielectric, such as gels, powders, or plastics, which would provide coupling to the surface but not necessarily cooling.

Microwave applicator 10 further includes at least one flexible, printed circuit board (PCB) 14. PCB 14 includes at least one dual concentric conductor aperture (DCC aperture) 15 antenna on the front surface of the PCB. Preferably, PCB 14 includes a plurality of DCC apertures 15 thereby forming an antenna array.

Preferably each DCC aperture 15 is square in shape comprising a small rim of PCB 14 ground plane (outer conducting edge) around an aperture (hole) in the ground plane, and a second similarly shaped but not necessarily identically shaped (concentric) inner conducting edge separated from the outer conducting edge by a gap or radiating slot 21. Preferably, these radiating slots 21 are between 0.1 mm and 1.0 cm wide. The DCC apertures may be alternatively triangular, hexagonal, round, or any other geometric shape that provides a centrally isolated patch 20 or thin conducting rim 26 inner conductor surrounded concentrically by an open gap and similarly but not necessarily identically shaped outer conductor. In a preferred embodiment, PCB 14 consists of a flexible PCB material with two or more layers of copper foil and one or more layers of dielectric substrate. Such flexible PCBs are known in the art. A suitable example of such a PCB is available from Rogers Corp. located in Chandler, Arizona. The DCC apertures 15 are generally created with an etching process wherein copper is etched from the dielectric substrate in order to define the radiating slots 21, or the copper is electrodeposited in the desired pattern on suitable dielectric substrate.

Located on the back surface of the PCB are a plurality of microstrip feed lines 22 that are defined by etching and that are coupled to the DCC apertures 10 and to a plurality of couplers 23. In a preferred embodiment, the couplers 23 consist of coaxial type connectors for coupling to coaxial cables 24 having mating coaxial connectors. Coaxial cables 24 are coupled to at least one of an external microwave device which consists of either at least one of a microwave power source 71 for supplying microwave power to PCB 14 and thereby to the DCC apertures 15, or at least one of a radiometer circuit or high gain microwave receiver 70 for amplifying the microwave signal received by the microwave applicator from superficial tissue. Power is supplied to the DCC apertures by the microstrip feed lines 22. Alternatively, the received signal from tissue may be supplied to the high gain microwave receiver 70 by the microstrip feed lines 22.

Alternatively, the DCC apertures and subsequent antenna array may be constructed from a soft fabric dielectric material (e.g. GORE-TEX or PTFE fabric) with metalization electrodeposited in a correct array design onto both sides of the soft fabric before attaching or forming the array fabric to the bolus container.

Additionally, three or more metal layers and two or more substrates may be used in forming PCB 14 that may provide useful enhancements for some applications, such as improved shielding of electromagnetic fields in air behind the microwave applicator, and allow the use of stripline instead of microstrip style feedlines. . A three or more layer PCB may be useful for multi-layer overlapping or concentrically mounted antennas to facilitate higher resolution microwave imaging of temperature dependent signals radiated back from heated tissue toward the array surface (i.e., microwave radiometry). Thus, some or all of the DCC apertures 15 would be used to heat tissue, while DCC or other shape antennas (e.g. spirals 17 or squares 18) formed in the multiple PCB 14 layers would be available for sensing temperature from the tissue for feedback control of power supplied to the heating DCC apertures 15.

Microwave applicator 10 further includes a soft and flexible attachment material 30 such as, for example, stretchable elastic fabric (e.g. spandex), cotton fabric, polyester fabric, or other suitable soft and flexible fabric that is at least attached to PCB 14 and bolus 11. Preferably, it is placed over one or both PCB 14 and bolus 11 to secure the entire microwave applicator 10 in place over a target region, thereby forming the microwave applicator 10 into a type of garment which closely conforms to target surfaces of the object (e.g. parts of human anatomy) to be heated. Preferably, flexible material 30 is coupled either to itself or to PCB 14 and/or to bolus 11 with simple adjustable and quick release fasteners such as, for example, Velcro, nylon quick release strap fasteners 35, and other similar type fasteners, or continuous (e.g. tubular) elastic fabric. Likewise, a combination of fasteners may be used to secure the flexible material 30 of the microwave applicator 10 to the target surface to be heated.

In accordance with one feature of the present invention, flexible material 30 is arranged to configure the microwave applicator 10 into a comfortable garment-like unit such as, for example, a vest, jacket, shorts, cap, hood, blanket, custom shaped conformal wrap, or sleeve for placement over a torso, shoulder, hips, scalp, face, or an appendage, such as for example an arm, leg or finger.

Alternatively, the microwave applicator may be configured for placement within a body cavity, for example by being wrapped around a probe or similar device, for treating tissue or organs within 1–1.5 cm distance around a natural body cavity. Such a configuration may require a different, sterile flexible material 30 which applies outward elastic force (e.g. sponge like) against the microwave applicator 10 and cavity wall rather than inward elastic pressure against the microwave applicator 10 and target surface.

Figure 3:
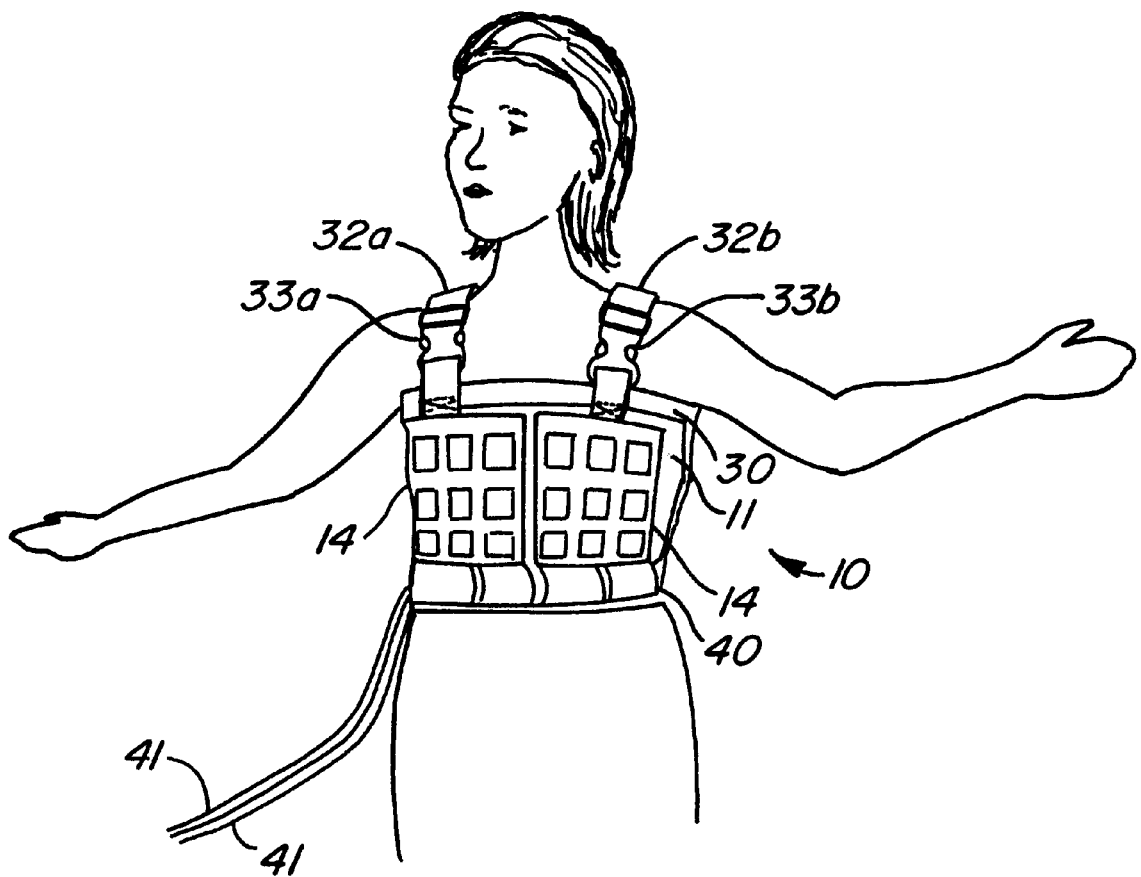
FIG. 3 is a front perspective view of a microwave applicator in accordance with the present invention.
Figure 4A:
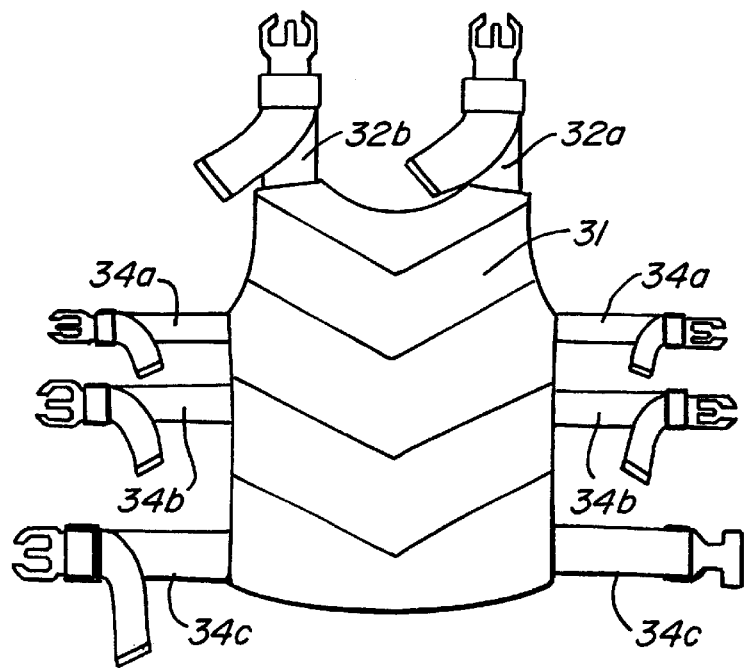
FIGS. 4A and 4B are back elevation views of a microwave applicator illustrated in FIG. 3.
Figure 4B:
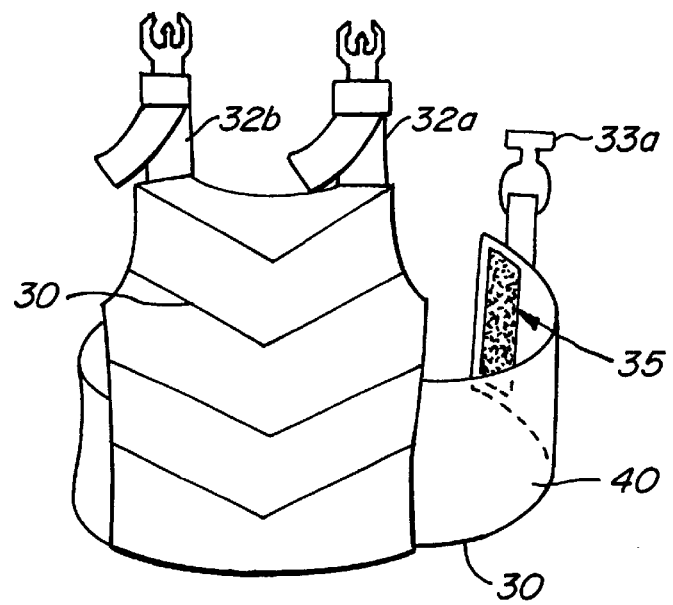
Figure 5:
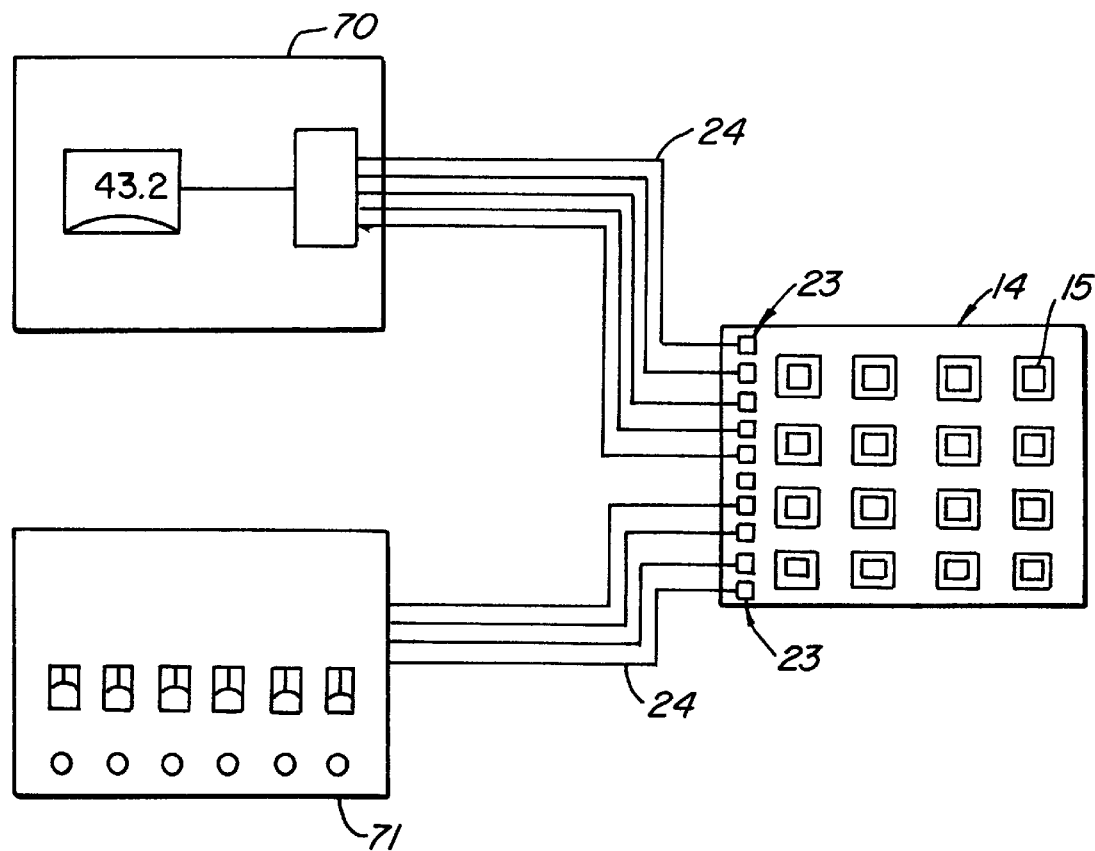
FIG. 5 is a schematic illustration of a PCB for use with a microwave applicator in accordance with the present invention coupled to microwave sources.
Figure 6:
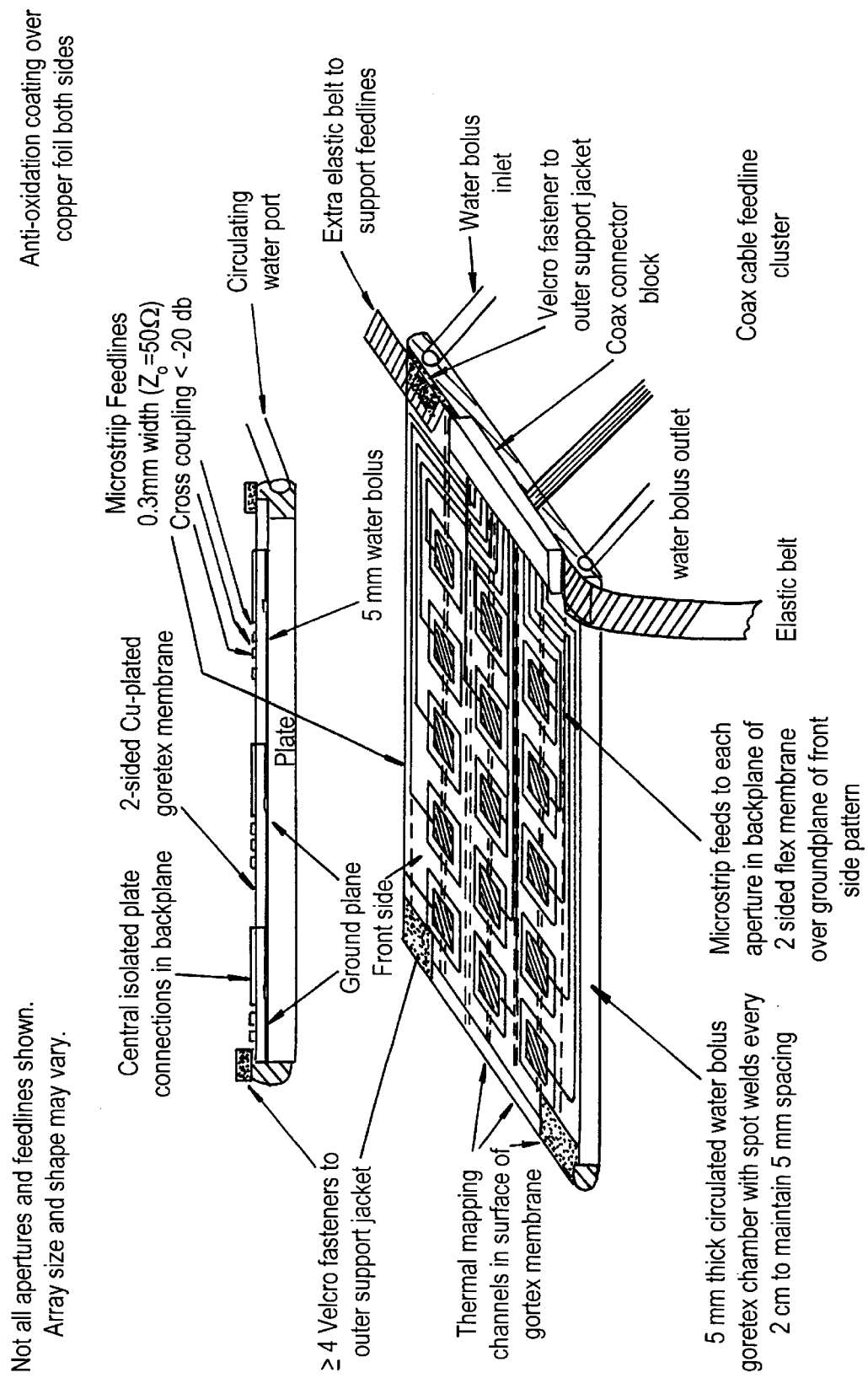
FIG. 6 is a perspective view of a microwave applicator in accordance with the present invention.
Figure 7:
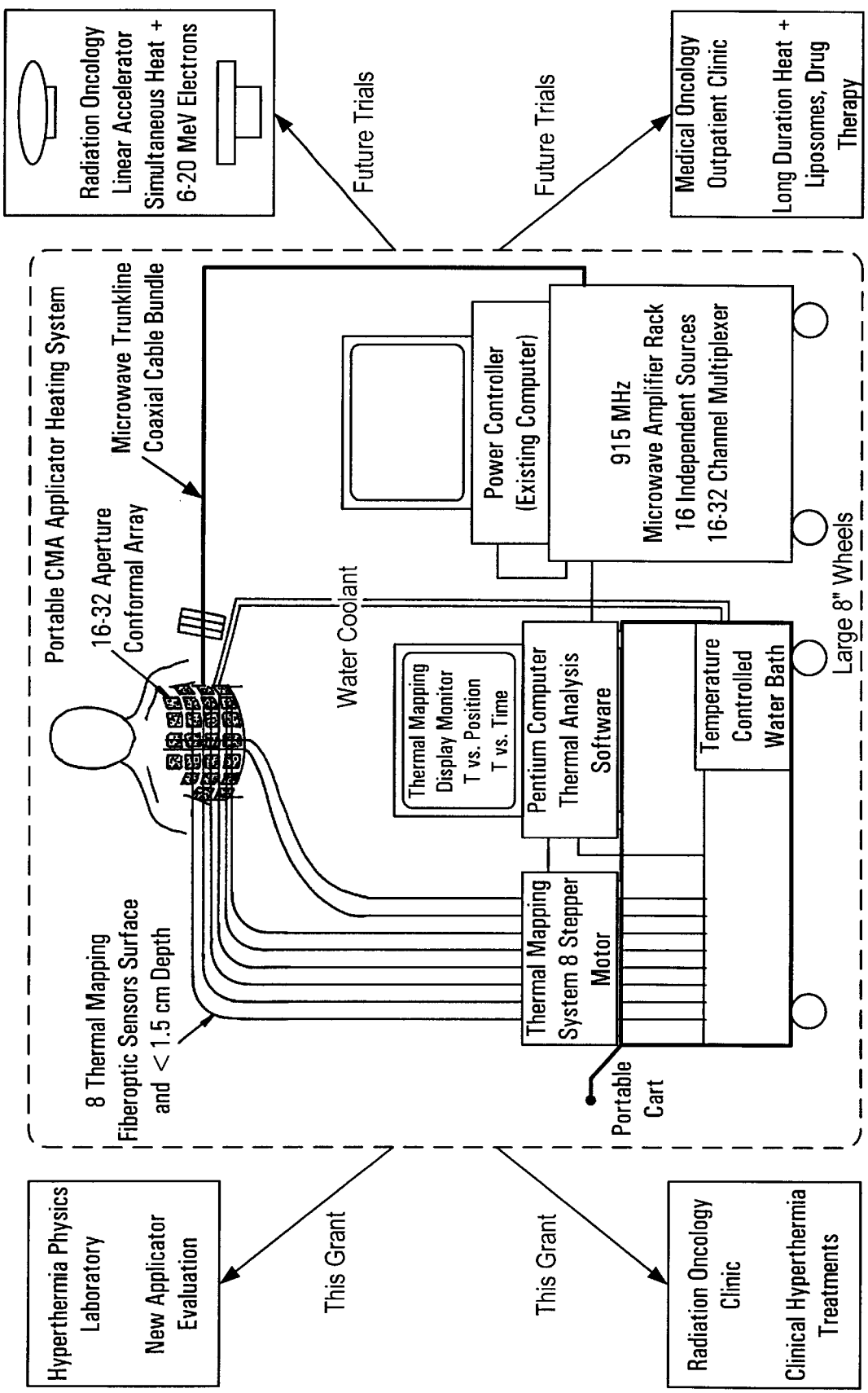
FIG. 7 is a schematic illustration of an arrangement using a microwave applicator in accordance with the present invention.
Figure 8:
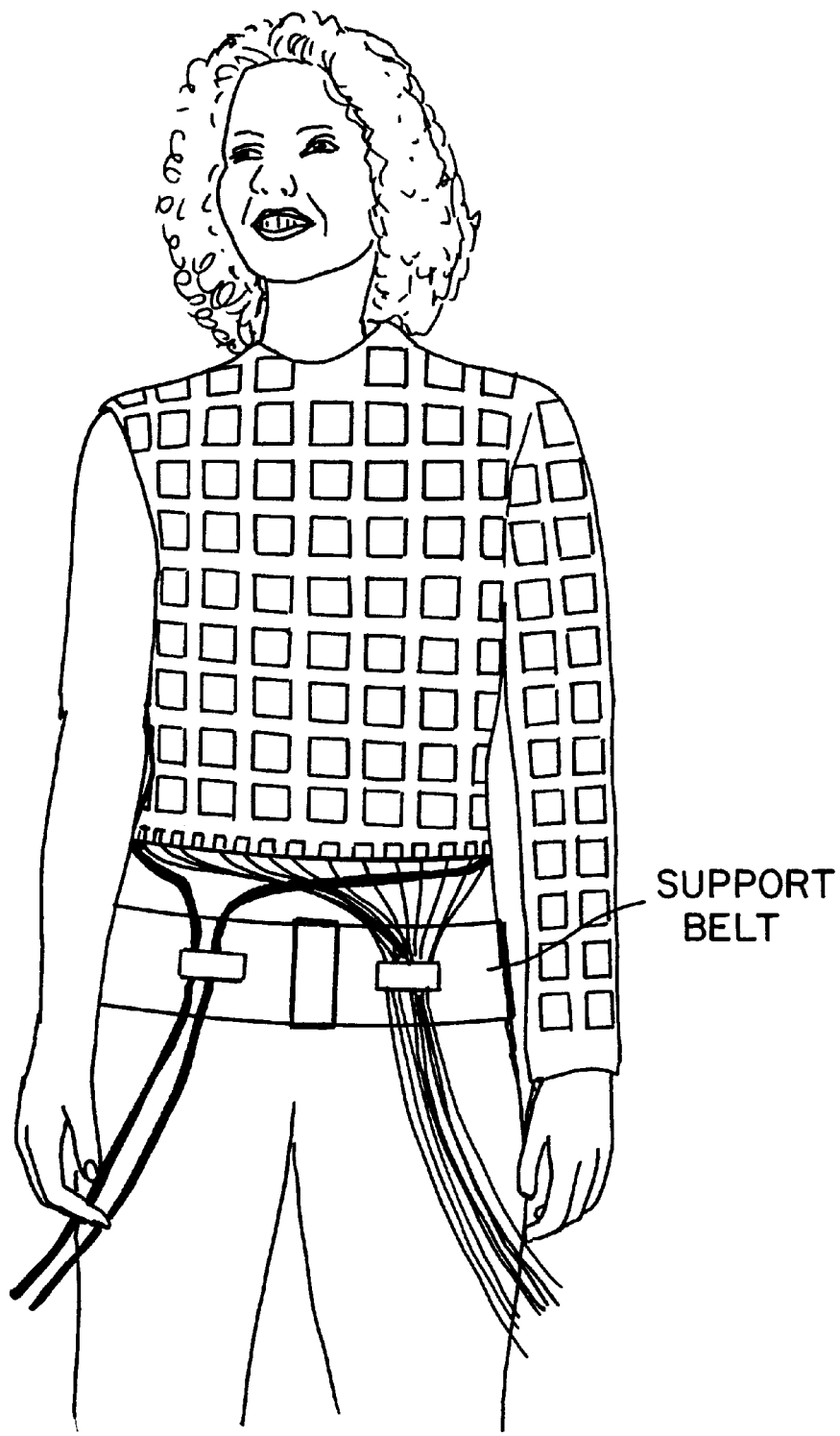
FIG. 8 is a front view of the microwave applicator configured as a jacket.
Figure 9:
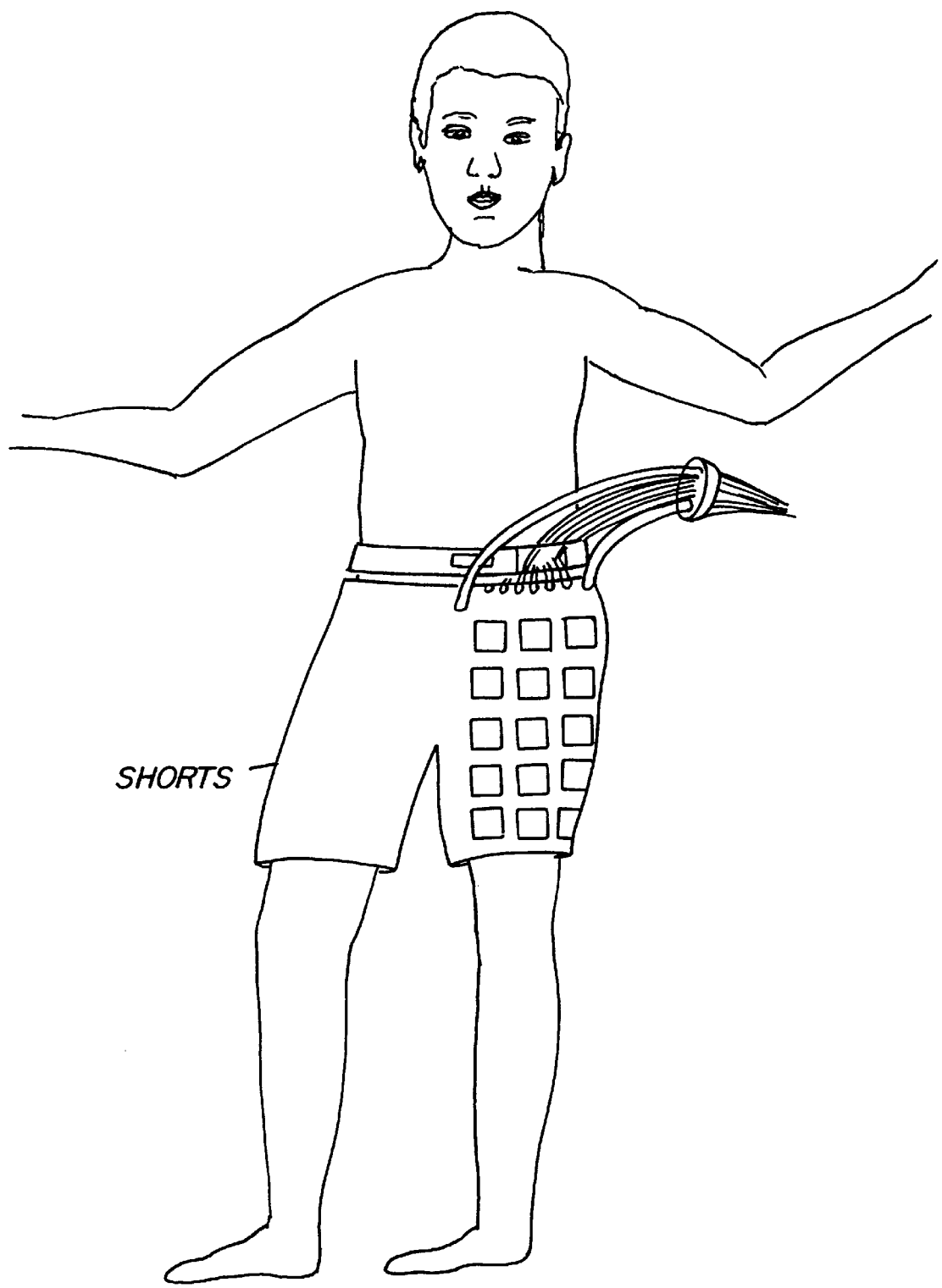
FIG. 9 is a front view of the microwave applicator configured as a pair of shorts.
Figure 10:
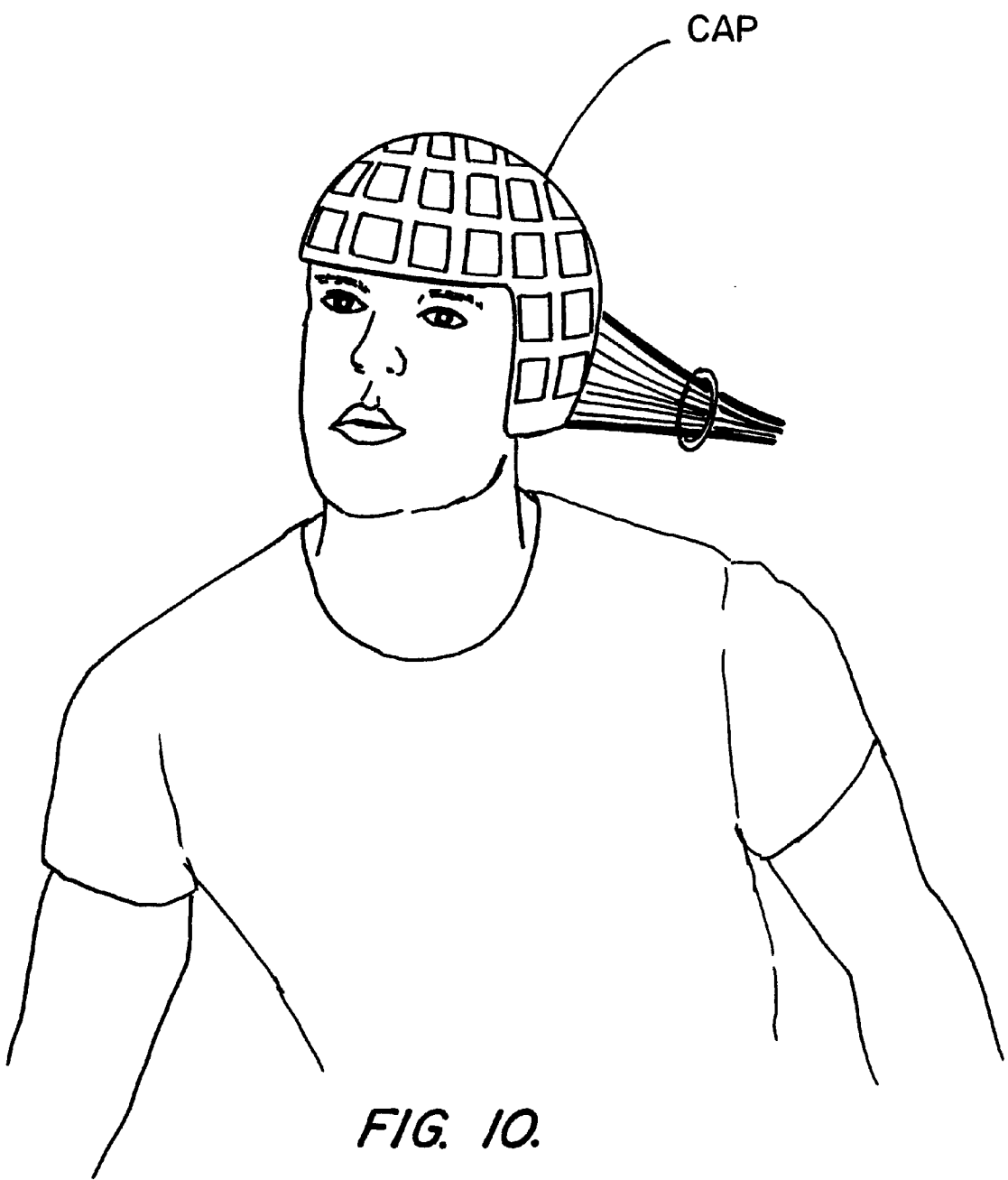
FIG. 10 is a front view of the microwave applicator configured as a cap.
Figure 11:
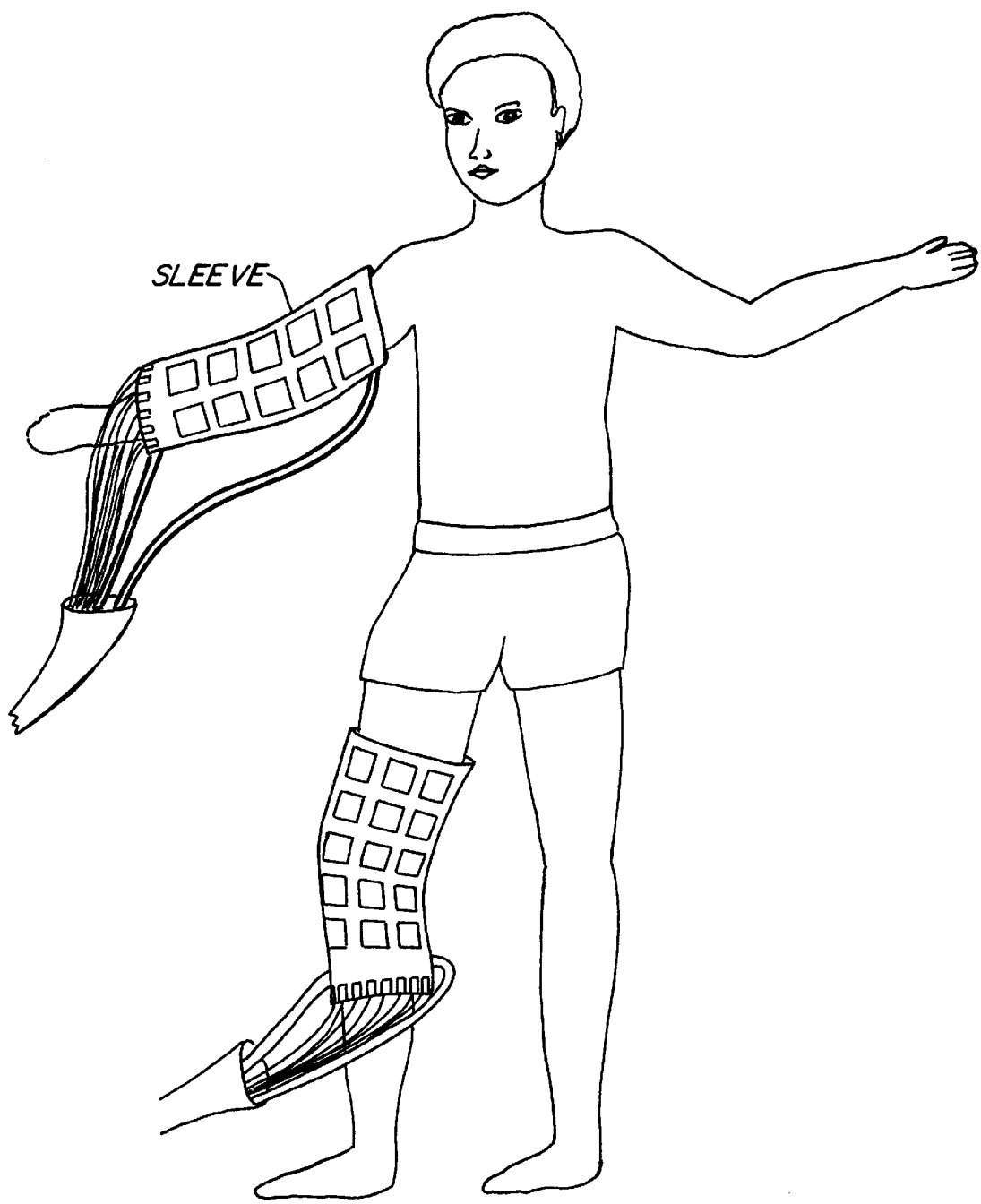
FIG. 11 is a front view of the microwave applicator configured as a custom shaped informal wrap.

FIGS. 3 and 4 illustrate the microwave applicator configured as a vest or jacket that may include more than one PCB 14. As can be seen, the microwave applicator 10 is secured over the target surface on the front of the vest by attachment material 30 and may be connected to a separate back 31 of the vest. Two adjustable length straps 32 a, b extend from back 31 and are coupled with, for example, quick release snaps 33 a, b to the front of the vest that contains or supports microwave applicator 10. Further elastic fasteners 34 may be included as needed or desired to provide consistent inward force snugly and comfortably holding the microwave applicator 10 to a patient while allowing movements (ie. chest moving in and out during breathing, stomach shifting during walking or changing positions). While strap and buckle fasteners may be preferred for rapid adjustment of the vest at the top (over shoulders), tubular elastic material (e.g. spandex shirt) or a wide elastic belt (sash) fasteners 34 should be preferable for attachment of the microwave applicator 10 around the upper torso to maintain more consistent inward pressure against the microwave applicator 10 and target surface in areas where there is movement.

Bolus 11 includes a tissue-engaging surface 50 which engages the tissue or skin of the subject patient. Opposite the tissue-engaging surface 50 is the non-tissueengaging surface 51 which is adjacent to or engages the front surface of PCB 14. In accordance with one of the advantages of the present invention, bolus 11 is relatively thin and thus is generally between 0.25 cm to 2.5 cm in thickness T. Preferably, the bolus has a thickness T in a range of 0.5 cm to 1.5 cm and most preferably, has a thickness T of approximately 0.75 cm. Although other flexible dielectrics may be used, preferably bolus compartment 11 is filled with dielectric fluid (e.g. high dielectric constant water or low dielectric constant silicone oil) which is circulated vigorously through the bolus compartment through fluid tubing 25 which communicates with a temperature controlled circulation bath chamber (not shown). Other dielectrics include, for example, low loss solid flexible plastic, and a powered or gel type dielectric.

In accordance with another feature of the present invention, a support belt 40 is included. Support belt 40 may be separate or integral with the flexible attachment material 30, i.e., part of the vest, jacket, etc. Support belt 40 includes attachment fittings 41 for quick release fixation of microwave coaxial cables 24 which carry microwave signals to and from external microwave devices through couplers 23 of PCB 14, and tubing connections 25 to the temperature regulated water or other dielectric fluid supply. The support belt 40 supports the weight of these coaxial cables and fluid tubing conduits to allow patient ambulation during therapy.

Figure 2A:
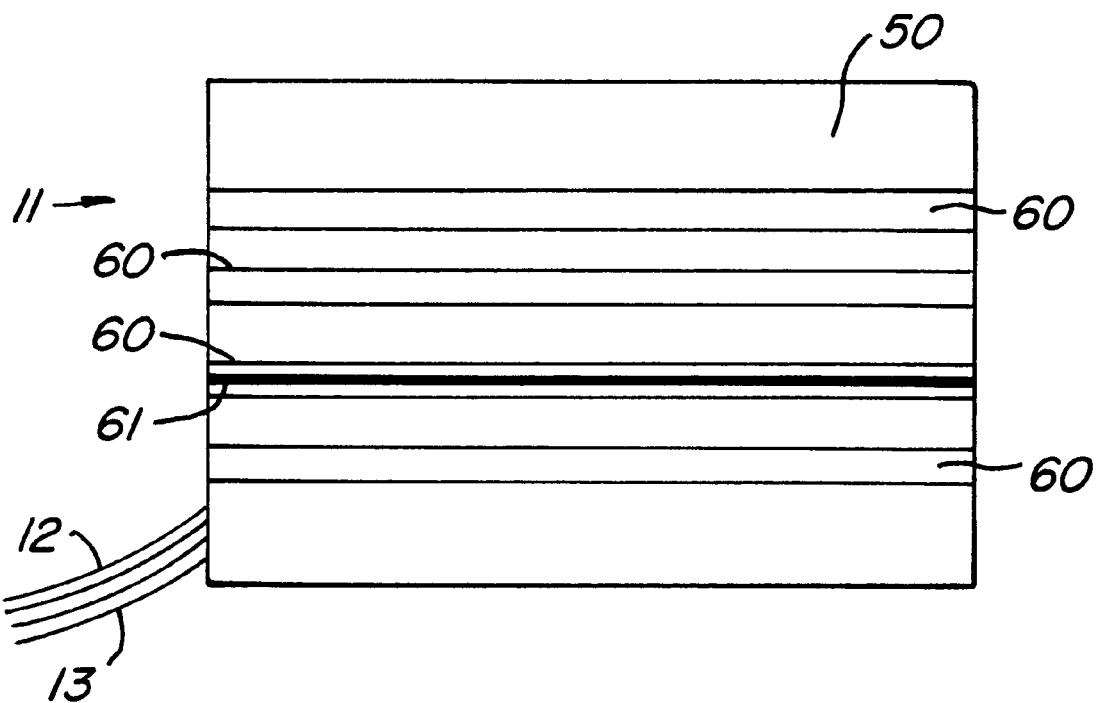
FIG. 2A is a front elevation view of a bolus for use with the present invention.
Figure 2B:
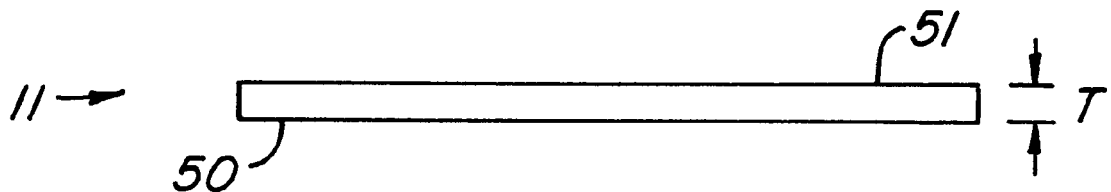
FIG. 2B is a side elevation view of the bolus illustrated in FIG. 2A.

In accordance with another embodiment of the present invention, non-invasive temperature monitoring structure is provided for monitoring the temperature of the superficial tissue. With reference to FIG. 2A, a first embodiment for the non-invasive temperature structure is shown. Bolus 11 includes at least one plastic catheter 60 molded into its tissue-engaging surface 50. At least one sensor 61 is placed within catheter 60. Preferably, sensor 61 is made from fiber optic or high resistance lead materials which minimize perturbation of the radiated field. Alternatively, the sensor 61 may be pulled repeatedly through the catheter to obtain temperature at many points along the catheter (e.g. 0.5–1.0 cm spacing of measurement points). Preferably, a plurality of plastic catheters 60 are provided and a plurality of sensors 61 are provided to identify tissue temperatures at regular intervals across the target tissue region surface .

In accordance with another embodiment of the present invention, the non-invasive temperature structure includes radiometric imaging capabilities. Preferably, the radiometric imaging capability results from either time multiplexed use of the same DCC aperture for heating tissue and receiving energy radiated back from the tissue, or from a complimentary antenna that is concentric with or overlaps at least one of the DCC thin rim apertures 26. Generally, such a complimentary antenna consists of a second smaller DCC aperture or a spiral or other shaped microstrip antenna located in the center of the front surface DCC thin conducting rim aperture 26, or in back layer(s) of the PCB 14 overlapping the front surface rim aperture 26.

By including temperature monitoring with the present invention, multiple microwave applicators may be used simultaneously with the same or multiple patients. By supplying temperature monitoring information to a computer automatic feedback control system (not shown), a single attendant, such as a doctor, nurse, or technologist may administer microwave applicator treatments to multiple patients simultaneously since the control system would be able to more adequately control operation of the microwave applicators with minimal operator intervention.

In practical use, once the microwave applicator has been assembled as a vest, for example, the vest is placed on a patient over the superficial target tissue. Because of the flexible nature of the microwave applicator 10 and its components, the vest is conformed in intimate contact with the contoured anatomy of the patient. Power is then supplied from the microwave power source and is applied to the PCB 14. The power is applied in a range of 0.1–10,000 Watts per DCC aperture 15 and preferably, in a range of 5–50 Watts per aperture 15 and most preferably, the amount of power supplied is less than 40 Watts per aperture 15. The power is applied either in short high power pulses or preferably, at a continuous wave frequency in the range of 300–5000 MHz, more preferably, in a range of 430–2450 MHz, and most preferably, at a continuous wave frequency of about 433 MHz or 915 MHz. Treatment is continued for a desired amount of time in accordance with a doctor's instructions, preferably, less than 1 second to 5 minutes for high power pulses, and more preferably, for durations of 30 minutes to 4 hours for moderate power, or for extended periods (e.g. overnight) at even lower average power levels.

Thus, the present invention provides a lightweight and flexible applicator for use in heating highly contoured large area tissue regions within 1–1.5 cm of the skin surface. The antenna array and the individual DCC apertures 15 may be arbitrarily arranged and sized for irregularly shaped small or very large surface area targets. By including an outer, elastic attachment material 30 for holding the PCB in place, and thereby configuring the microwave applicator into some type of appropriate garment, patients may sit or walk about the power supply with only one, somewhat large connection to the power supply and to the coolant supply. The resulting ultra-thin and flexible microwave applicator may be wrapped securely around highly contoured patient anatomy. A microwave applicator in accordance with the present invention is essentially radiation transparent, thus allowing for simultaneous heat and external beam radiation treatment.

Thus, patient comfort during the treatment is improved due to the thin, flexible and lightweight structure of the PCB antenna array 14 and corresponding bolus 11, as well as due to such features of the invention which allow the patient to move during heat treatment, such as standing, pacing, sitting reading a book, or lying in any position. The improved patient comfort resulting therefrom will allow for longer treatment times when such longer treatment times are beneficial.

While the microwave applicator of the present invention has been described for use in treating skin and superficial tissue, those skilled in the art will understand that such a microwave applicator and its DCC antenna array may also be used in a passive mode for tissue property measurements such as for monitoring subcutaneous tissue temperature, blood perfusion or flow dynamics, vascular permeability, or the extent and distribution of tissue necrosis or other heterogeneities of tissue dielectric properties such for example to diagnose cancer. Thus, there may be applications for using a microwave garment or vest in accordance with the present invention for monitoring tissue properties without producing any heat at all. The present invention provides a microwave applicator that applies microwaves to tissue.

Although the invention has been described with reference to specific exemplary embodiments, it will be appreciated that it is intended to cover all modifications and equivalents within the scope of the appended claims.

What is claimed is:

1. A flexible conformal microwave applicator, the applicator comprising:
   a flexible, dielectric containing compartment having a variable contour, tissue-engaging surface and an opposite, non-tissue-engaging surface;
   an antenna array adjacent to the non-tissue-engaging surface and comprising:
      at least one flexible printed circuit board comprising a front metal surface, a dielectric substrate, a back metal surface, and connection means for connecting the antenna array to at least one external microwave device;
      at least one dual concentric conductor (DCC) radiating aperture on the front surface; and
      at least one microstrip feedline in communication with the dual concentric conductor aperture and the connection means; and
   flexible attachment material for placement over the antenna array and dielectric compartment to allow the microwave applicator to be attached to a subject.

2. The microwave applicator of claim 1 wherein the antenna array comprises a plurality of dual concentric conductor radiating apertures on the front surface and a plurality of feedlines in communication with the dual concentric conductor radiating apertures and the connection means.

3. The microwave applicator of claim 1 further comprising non-invasive temperature monitoring means for monitoring the temperature of superficial tissue of the subject.

4. The microwave applicator of claim 3 wherein the temperature monitoring means comprises at least one plastic catheter molded into the tissue-engaging surface and at least one temperature sensor that is placed within or pulled repeatedly through the catheter.

5. The microwave applicator of claim 3 wherein the temperature monitoring means comprises radiometric imaging means located on the flexible printed circuit board.

6. The microwave applicator of claim 5 wherein the radiometric imaging means comprises at least one complimentary antenna that is located within a central portion of a DCC aperture.

7. The microwave applicator of claim 5 wherein the radiometric imaging means is accomplished by time-sequenced heating and sensing from at least one aperture of the at least one dual concentric conductor aperture.

8. The microwave applicator of claim 6 wherein the complimentary antenna comprises a second smaller dual concentric conductor aperture concentric within the central portion of a dual concentric conductor aperture.

9. The microwave applicator of claim 6 wherein the complimentary antenna comprises a microstrip antenna within the central portion of a dual concentric conductor aperture.

10. The microwave applicator of claim 6 wherein the complimentary antenna comprises a spiral microstrip antenna within the central portion of a dual concentric conductor aperture.

11. The microwave applicator of claim 5 wherein the radiometric imaging means comprises at least one complimentary antenna located in a metal layer of the printed circuit board that is different from the dual concentric conductor and at least partially overlaps a dual concentric conductor aperture.

12. The microwave applicator of claim 11 wherein the complimentary antenna comprises at least one spiral microstrip antenna that partially overlaps a dual concentric conductor aperture.

13. The microwave applicator of claim 1 further comprising a support belt to act as a strain relief and a support for connecting microwave coaxial cables and tubes for circulating cooling fluid.

14. The microwave applicator of claim 1 wherein the dielectric containing compartment has a thickness in a range of 0.25 cm to 2.5 cm.

15. The microwave applicator of claim 14 wherein the dielectric containing compartment has a thickness in a range of 0.5 cm to 1.5 cm.

16. The microwave applicator of claim 14 wherein the dielectric containing compartment has a thickness 0.75 cm.

17. The microwave applicator of claim 1 wherein the flexible attachment material is configured such that the microwave applicator is configured as a vest.

18. The microwave applicator of claim 1 wherein the flexible attachment material is configured such that the microwave applicator is configured as a jacket.

19. The microwave applicator of claim 1 wherein the flexible attachment material is configured such that the microwave applicator is configured as a custom shaped informal wrap.

20. The microwave applicator of claim 1 wherein the flexible attachment material is configured such that the microwave applicator is configured as a blanket.

21. The microwave applicator of claim 1 wherein the flexible attachment material is configured such that the microwave applicator is configured as a cap.

22. The microwave applicator of claim 1 wherein the flexible attachment material is configured such that the microwave applicator is configured as a sleeve.

23. The microwave applicator of claim 1 wherein the flexible attachment material is configured such that the microwave applicator is configured as a pair of shorts.

24. The microwave applicator of claim 1 wherein the external microwave devices are microwave power sources.

25. The microwave applicator of claim 1 wherein the external microwave devices are high gain microwave receivers.

26. A flexible conformal microwave applicator comprising:
a flexible bolus having a tissue-engaging surface and an opposite non-tissue-engaging surface;
an antenna array adjacent to the non-tissue-engaging surface and comprising:
at least one flexible printed circuit board comprising a front metal surface, a dielectric substrate, a back metal surface, and connection means for connecting the antenna array to a plurality of external microwave devices;
a plurality of dual concentric conductor (DCC) apertures on the front surface; and
a plurality of microstrip feedlines in communication with the dual concentric conductor apertures and the connection means; and
flexible attachment material for placement over the antenna array and bolus to allow the microwave applicator to be securely attached to a subject.

27. The microwave applicator of claim 26 further comprising non-invasive temperature monitoring means for monitoring the temperature of superficial tissue.

28. The microwave applicator of claim 27 wherein the temperature monitoring means comprises at least one plastic catheter or open lumen channel molded into the tissue-engaging surface and at least one temperature sensor that is within or pulled repeatedly through the catheter or open lumen channel.

29. The microwave applicator of claim 28 wherein the temperature monitoring means comprises a plurality of plastic catheters or channels molded into the tissue-engaging surface and a plurality of temperature sensors that are within or pulled repeatedly through the catheters.

30. The microwave applicator of claim 28 wherein the temperature monitoring means comprises radiometric imaging means located on the flexible printed circuit board.

31. The microwave applicator of claim 30 wherein the radiometric imaging means comprises at least one complimentary antenna that is located within or at least partially overlaps a central portion of a DCC radiating aperture and consists of one of a dual concentric conductor aperture.

32. The microwave applicator of claim 30 wherein the radiometric imaging means comprises at least one complimentary antenna that is located within or at least partially overlaps a central portion of a DCC radiating aperture and consists of one of a microstrip antenna.

33. The microwave applicator of claim 30 wherein the radiometric imaging means comprises at least one complimentary antenna that is located within or at least partially overlaps a central portion of a DCC radiating aperture and consists of one of a spiral microstrip antenna.

34. The microwave applicator of claim 30 wherein the radiometric imaging means is accomplished by time-sequenced heating and sensing from at least one of the dual concentric conductor apertures.

35. The microwave applicator of claim 26 further comprising a support belt to act as a strain relief and support for connecting microwave coaxial cables and circulating cooling fluid tubes.

36. The microwave applicator of claim 26 wherein the fluid compartment has a thickness in a range of 0.25 cm to 2.5 cm.

37. The microwave applicator of claim 36 wherein the fluid compartment has a thickness in a range of 0.5 cm to 1.5 cm.

38. The microwave applicator of claim 37 wherein the fluid compartment has a thickness of 0.75 cm.

39. The microwave applicator of claim 26 wherein the flexible attachment material is configured such that the microwave applicator is configured as a vest.

40. The microwave applicator of claim 26 wherein the flexible attachment material is configured such that the microwave applicator is configured as a jacket.

41. The microwave applicator of claim 26 wherein the flexible attachment material is configured such that the microwave applicator is configured as a custom shaped conformal wrap.

42. The microwave applicator of claim 26 wherein the flexible attachment material is configured such that the microwave applicator is configured as a blanket.

43. The microwave applicator of claim 26 wherein the flexible attachment material is configured such that the microwave applicator is configured as a sleeve.

44. The microwave applicator of claim 26 wherein the flexible attachment material is configured such that the microwave applicator is configured as a pair of shorts.

45. The microwave applicator of claim 26 wherein the flexible attachment material is configured such that the microwave applicator is configured as a cap.

46. A method of heating and monitoring superficial tissue over contoured anatomy, the method comprising:
providing a microwave applicator comprising:
a flexible, dielectric-containing compartment having a tissue-engaging surface and an opposite non-tissue-engaging surface;

an antenna array adjacent to the non-tissue-engaging surface and comprising:
  at least one flexible printed circuit board comprising a front metal surface, a dielectric substrate, a back metal surface, and connection means for connecting the antenna array to at least one external microwave device;
  at least one dual concentric conductor aperture on the front surface; and
  at least one microstrip feedline in communication with the dual concentric conductor aperture and the connection means; and
flexible attachment material for placement over the antenna array and dielectric compartment to allow the microwave applicator to be securely attached to a subject;
placing the microwave applicator over the target tissue on a subject;
conforming the microwave applicator to fit the contour of the patient anatomy to be treated; and
supplying power from the power source to the at least one connection means and thereby to the at least one microstrip feedline and the at least one dual concentric conductor radiating aperture; and creating a radiating microwave field within the contoured anatomy of the patient with the at least one dual concentric conductor aperture to thereby heat superficial tissue located directly under the corresponding radiating aperture.

47. The method of claim 46 with the method further comprising
non-invasive monitoring of physiologic tissue properties.

48. The method of claim 46 wherein the amount of power supplied is in a range of 0.1–10,000 Watts per aperture.

49. The method of claim 46 wherein the amount of power supplied is continuous wave in a range of 5–50 Watts per aperture.

50. The method of claim 46 wherein the amount of power supplied is continuous wave less than 35 Watts per aperture.

51. The method of claim 46 wherein the power is applied at a frequency in a range of 300–5000 MHz.

52. The method of claim 51 wherein the power is continuous wave applied at a frequency in a range of 400–2500 MHz.

53. The method of claim 52 wherein the power is continuous wave applied at a frequency of 915 MHz.

54. The method of claim 46 further comprising simultaneous heating and non-invasive monitoring of physiologic tissue properties..

55. The method of claim 54 wherein the monitoring of the temperature or other physiologic property is accomplished by radiometric imaging.

56. The method of claim 46 wherein the microwave applicator comprises a plurality of dual concentric conductor apertures and a plurality of microstrip feedlines.

57. The method of claim 46 wherein the microwave applicator comprises a plurality of dual concentric conductor apertures, a plurality of complimentary microstrip antenna structures, and a plurality of microstrip feedlines connected to the connection means.

58. The method of claim 57 wherein the amount of power supplied is less than 50 Watts per aperture.

59. The method of claim 57 further comprising monitoring changes in physiologic tissue properties of the superficial tissue.

60. The method of claim 59 wherein the monitoring of physiologic tissue properties is accomplished by radiometric imaging.

* * * * *